(12) United States Patent
Cohen et al.

(10) Patent No.: US 8,748,378 B2
(45) Date of Patent: Jun. 10, 2014

(54) THERAPIES FOR ACUTE RENAL FAILURE

(75) Inventors: Charles M. Cohen, Weston, MA (US); Kuber T. Sampath, Holliston, MA (US); Slobodan Vukicevic, Zagreb (HR)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 13/079,161

(22) Filed: Apr. 4, 2011

(65) Prior Publication Data

US 2011/0257093 A1 Oct. 20, 2011

Related U.S. Application Data

(63) Continuation of application No. 12/583,013, filed on Aug. 11, 2009, now abandoned, which is a continuation of application No. 09/445,328, filed as application No. PCT/US98/03197 on May 5, 1998, now abandoned.

(60) Provisional application No. 60/045,619, filed on May 5, 1997.

(51) Int. Cl.
  *A61K 38/17* (2006.01)
  *A61P 13/12* (2006.01)
  *C07K 14/51* (2006.01)

(52) U.S. Cl.
  USPC ........... 514/8.8; 514/15.4; 530/350; 623/23.7

(58) Field of Classification Search
  None
  See application file for complete search history.

(56) References Cited

U.S. PATENT DOCUMENTS

| | | | |
|---|---|---|---|
| 4,237,167 A | 12/1980 | Cavazza | |
| 4,627,839 A | 12/1986 | Young | |
| 5,011,691 A | 4/1991 | Oppermann et al. | |
| 5,013,649 A | 5/1991 | Wang et al. | |
| 5,045,452 A | 9/1991 | Spragg et al. | |
| 5,266,683 A | 11/1993 | Oppermann et al. | |
| 5,525,621 A * | 6/1996 | Burt et al. | 514/393 |
| 5,714,511 A | 2/1998 | Saavedra et al. | |
| 5,723,441 A | 3/1998 | Higley et al. | |
| 5,820,589 A | 10/1998 | Torgerson | |
| 5,849,686 A | 12/1998 | Kuberasampath et al. | |
| 5,879,908 A | 3/1999 | Laping et al. | |
| 6,077,823 A * | 6/2000 | Kuberasampath et al. | 514/1.5 |
| 6,120,760 A | 9/2000 | Hotten et al. | |
| 6,194,376 B1 | 2/2001 | Kuberasampath et al. | |
| 6,288,031 B1 | 9/2001 | Kuberasampath et al. | |
| 6,407,060 B1 | 6/2002 | Charette et al. | |
| 6,498,142 B1 | 12/2002 | Sampath et al. | |
| 6,861,404 B1 | 3/2005 | Cohen et al. | |
| 7,056,882 B2 | 6/2006 | Kuberasampath et al. | |
| 7,147,839 B2 | 12/2006 | Sampath et al. | |
| 7,196,056 B2 | 3/2007 | Cohen et al. | |
| 7,524,817 B2 | 4/2009 | Cohen et al. | |
| 8,017,580 B2 | 9/2011 | Cohen et al. | |

FOREIGN PATENT DOCUMENTS

| | | |
|---|---|---|
| CA | 1128881 | 8/1982 |
| JP | 04-026624 | 1/1992 |
| WO | WO 88/00205 | 1/1988 |
| WO | WO 90/11366 | 10/1990 |
| WO | WO 91/18098 | 11/1991 |
| WO | WO 92/00067 | 1/1992 |
| WO | WO 92/15323 | 9/1992 |
| WO | WO 93/04692 | 3/1993 |
| WO | WO 93/05172 | 3/1993 |
| WO | WO 93/05751 | 4/1993 |
| WO | WO 94/03075 | 2/1994 |
| WO | WO 94/03200 | 2/1994 |
| WO | WO 94/03600 | 2/1994 |
| WO | WO 94/06449 | 3/1994 |
| WO | WO 94/10203 | 5/1994 |
| WO | WO 94/20539 | 9/1994 |
| WO | WO 95/08621 | 3/1995 |
| WO | WO 95/11983 | 5/1995 |
| WO | WO 95/33830 | 12/1995 |
| WO | WO 97/41880 | 11/1997 |
| WO | WO 97/41881 | 11/1997 |

OTHER PUBLICATIONS

Simic et al. Bone morphogenetic proteins in development and homeostasis of kidney. Cytokine Growth Factor Rev. Jun. 2005;16(3):299-308.*
Anderson et al., "Acute renal failure," *Harrison's principles of internal medicine*, 9th ed., Isselbacher et al. (Eds.), Chpt. 275, p. 1293-1299 (New York: McGraw-Hill, 1980).
Asahina et al., "Human osteogenic protein-1 induces both chondroblastic and osteoblastic differentiation of osteoprogenitor cells derived from newborn rat calvaria," *J. Cell. Biol.*, 123(4):921-933 (1993).
Avner, "Polypeptide growth factors in metanephric growth and segmental nephron differentiation," *Pediatr. Nephrol.*, 4:372-377 (1990).
Bard et al., "Towards a genetic basis for kidney development," *Mech. Develop.*, 48:3-11 (1994).
Basic, "The role of bone morphogenetic proteins in renal compensatory growth," LijecnickiVjesnik,HR, Urednistvo Lijecnickog Vjesnika; Zagreb, 119(2):53-55 (1997) ISSN: 0024-3477, CODEN: LIVJA5.
Border et al., "Suppression of experimental glomerulonephritis by antiserum against transforming growth factor β1," *Nature*, 346:371-374 (1990).
Bowie et al., "Deciphering the message in protein sequences: tolerance to amino acid substitutions," *Science*, 247:1306-1310 (1990).
Brady et al., "Acute renal failure," *Harrison's principles of internal medicine*, 13th ed., Isselbacher et al. (Eds.), Chpt. 236, pp. 1265-1274 (New York: McGraw-Hill, 1994).

(Continued)

*Primary Examiner* — David Romeo
(74) *Attorney, Agent, or Firm* — Ropes & Gray LLP; James F. Haley, Jr.; Karen Mangasarian (57) ABSTRACT

The present invention provides methods for the treatment, and pharmaceuticals for use in the treatment, of mammalian subjects in, or at risk of, acute renal failure, or subject to, or at risk of, inflammation, neutrophil-mediated cell damage, and apoptosis resulting from tissue damage or injury. The methods involve the administration of certain proteins of the osteogenic protein/bone morphogenetic protein (OP/BMP) family within the TGF-β superfamily of proteins.

8 Claims, 2 Drawing Sheets

(56) References Cited

OTHER PUBLICATIONS

Brenner et al., "Chronic renal failure," *Harrison's principles of internal medicine*, 13th ed., Isselbacher et al. (Eds.), Chpt. 238, pp. 1274-1281 (New York: McGraw-Hill, 1994).
Carpenter et al., "Dialysis and transplantation in the treatment of renal failure," *Harrison's principles of internal medicine*, 13th ed., Isselbacher et al. (Eds.), Chpt. 238, pp. 1281 (New York: McGraw-Hill, 1994).
Celeste et al., "Identification of transforming growth factor beta family members present in bone-inductive protein purified from bovine bone," *Proc. Natl. Acad. Sci. (USA)*, 87:9843-9847 (1990).
Coe et al., "Approach to the patient with diseases of the kidneys and urinary tract," *Harrison's principles of internal medicine*, 13th ed., Isselbacher et al. (Eds.), Chpt. 237, pp. 1252 (New York: McGraw-Hill, 1994).
Dudley et al., "A requirement for bone morphogenetic protein-7 during development of the mammalian kidney and eye," *Genes & Devel.*, 9:2795-2807 (1995).
Floege et al., "Glomerular cells, extracellular matrix accumulation, and the development of glomerulosclerosis in the remnant kidney model," *Laboratory Investigation*, 66(4):485-497 (1992).
Glassock, "Immunosuppressive treatment in the prevention of renal failure in primary glomerular diseases," *Clin. Exp. Dial. Apheresis*, 5(1-2):21-46 (1981).
Glassock et al., "Immunopathogenic mechanisms of renal injury," *Harrison's principles of internal medicine*, 13th ed., Isselbacher et al. (Eds.), Chpt. 239, pp. 1292-1295 (New York: McGraw-Hill, 1994).
Guler et al., "Effects of recombinant insulin-like growth factor I on insulin secretion and renal function in normal human subjects," *Proc. Natl. Acad. Sci. (USA)*, 86:2868-2872 (1989).
Hamaguchi et al., "Transforming growth factor-$\beta$1 expression and phenotypic modulation in the kidney of hypertensive rats," *Hypertension*, 26(1):199-207 (1995).
Hirschberg et al., "Effects of insulin-like growth factor I on renal function in normal men," *Kidney Intl.* 43:387-397 (1993).
Jennerholm et al., "Magnetic resonance imaging of the transplanted kidney. Correlation to function and histopathology," *Acta Radiologica*, 31(5):499-503 (1990).
Jones et al., "Involvement of bone morphogenetic protein-4 (BMP-4) and Vgr-1 in morphogenesis and neurogenesis in the mouse," *Development*, 111:531-542 (1991).
Kees-Folts et al., "Relationship between hyperlipidemia, lipid mediators, and progressive glomerulosclerosis in the nephrotic syndrome," *Am. J. Nephrol.*, 13(5):365-375 (1993).
Kelly et al., "Intercellular adhesion molecule-1-deficient mice are protected against ischemic renal injury," *J. Clin. Invest.*, 97(4):1056-63 (1996).
Klahr et al., "The progression of renal disease," *N. Eng. J. Med.*, 318(25):1657-1666 (1988).
Kopple, "The rationale for the use of growth hormone or insulin-like growth factor I in adult patients with renal failure," *Miner. Electrolyte Metab.*, 18:269-275 (1992).
Lefer et al., "Anti-ischaemic and endothelial protective actions of recombinant human osteogenic protein (hOP-1)," *J. Mol. Cell. Cardiol.*, 24(6):585-593 (1992).
Lemann et al., "Use of the serum creatinine to estimate glomerular filtration rate in health and early diabetic nephropathy. Collaborative Study Group of Angiotensin Converting Enzyme Inhibition in Diabetic Nephropathy," *Am. J. Kidney Dis.*, 3:236-243 (1990).
Luo et al., "BMP-7 is an inducer of nephrogenesis, and is also required for eye development and skeletal patterning," *Genes & Devel.*, 9:2808-2820 (1995).
Massague, "The transforming growth factor-beta family," *Annu. Rev. Cell Biol.*, 6:597 (1990).
Miller et al., "Effects of IGF-I on renal function in end-stage chronic renal failure," *Kidney Intl.*, 46:201-207 (1994).
Needleman et al., "A general method applicable to the search for similarities in the amino acid sequence of two proteins," *J. Mol. Biol.*, 48:443-453 (1970).
Ngo et al., "Computational complexity, protein structure prediction, and the Levinthal Paradox," *The Protein Folding Problem and Tertiary Structure Prediction*, Merz and Le Grand (Eds) Springer Verlag, 433:492-495 (1994).
Ozkaynak et al., "OP-1 cDNA encodes an osteogenic protein in the TGF-beta family," *EMBO J.*, 9:2085-2093 (1990).
Ozkaynak et al., "Murine osteogenic protein (OP-1): High levels of mRNA in kidney," *Biochem. Biophys. Res. Comm.*, 179(1):116-123 (1991).
Ozkaynak et al., "Osteogenic protein-2: A new member of the transforming growth factor-$\beta$ superfamily expressed early in embryogenesis," *J. Biol. Chem.*, 267(35):25220-25227 (1992).
Ponticelli et al., "Conventional treatment of idiopathic nephrotic syndrome and membranous nephropathy in adults," *Clin. Nephrol.*, 35(S1):S16-S21 (1991).
Samaan et al., "Growth hormone levels in severe renal failure," *Metabolism*, 19(2):102-113 (1970).
Sampath et al., "Dissociative extraction and reconstitution of extracellular matrix components involved in local bone differentiation," *Proc. Natl. Acad. Sci. (USA)*, 78:7599-7603 (1981).
Sampath et al., "Bovine osteogenic protein is composed of dimers of OP-1 and BMP-2A, two members of the transforming growth factor-beta superfamily," *J. Biol. Chem.*, 265:13198-13205 (1990).
Sampath et al., "Recombinant human osteogenic protein-1 (hOP-1) induces new bone formation in vivo with a specific activity comparable with natural bovine osteogenic protein and stimulates osteoblast proliferation and differentiation in vitro," *J. Biol. Chem.*, 267(28):20352-20362 (1992).
Schiller et al., "Focal glomerulosclerosis in the remnant kidney model—an inflammatory disease mediated by cytokines," *Nephrology, Dialysis, Transplantation*, 12(3):430-437 (1997).
Shankland et al., "Expression of transforming growth factor-$\beta$1 during diabetic renal hypertrophy," *Kidney Intl.*, 46:430-442 (1994).
Tamaki et al., "TGF-$\beta$1 in glomerulosclerosis and interstitial fibrosis of adriamycin nephropathy," *Kidney Intl.*, 45:525-536 (1994).
Toback, "Regeneration after acute tubular necrosis," *Kidney Intl.*, 41:226-246 (1992).
Tolins et al., "Mechanisms of hypertensive glomerular injury," *Am. J. Cardiol.*, 62(11):54G-58G (1988).
Vukicevic et al., "Localization of osteogenic protein-1 (Bone Morphogenetic Protein-7) during human embryonic development: High affinity binding to basement membranes," *Biochem. Biophys. Res. Comm.*, 198(2):693-700 (1994).
Vukicevic et al., "Developing human lung and kidney are major sites for synthesis of bone morphogenetic protein-3 (Osteogenin)," *J. Histochem. Cytochem.*, 42(7):869-875 (1994).
Vukicevic et al., "Induction of nephrogenic mesenchyme by osteogenic protein 1 (bone morphogenetic protein 7)," *Proc. Natl. Acad. Sci. (USA)*, 93(17):9021-9026 (1996).
Vukicevic et al., "Recombinant human OP-1 (BMP-7) prevents rapid loss of glomerular function and improves mortality associated with chronic renal failure," *J. Am. Soc. Nephrol.*, 7(9):1867 (1996).
Watanabe et al., "Production of hydrogen peroxide by neutrophilic polymorphonuclear leukocytes in patients with diabetic nephropathy," *J. Clin. Lab. Anal.*, 7(4):209-213 (1993).
Wozney et al., "Novel regulators of bone formation: Molecular clones and activities," *Science*, 242:1528-1534 (1988).
Wright et al., "Serum-growth hormone and glucose intolerance in renal failure," *The Lancet*, 2:798-800 (1968).
Yamamoto et al., "Expression of transforming growth factor $\beta$ is elevated in human and experimental diabetic nephropathy," *Proc. Natl. Acad. Sci. (USA)*, 90:1814-1818 (1993).
Yamamoto et al., "Sustained expression of TGF-$\beta$1 underlies development of progressive kidney fibrosis," *Kidney Intl.*, 45:916-927 (1994).
Yang et al., "Local macrophage and myofibroblast proliferation in progressive renal injury in the rat remnant kidney," *Nephrology, Dialysis, Transplantation*, 13(8):1967-1974 (1998).
Creative Biomolecules Inks Deals with Purdue, Stryker—OP-1 a Major Focus, Biotech. Law Report 15(4):616-617 (1996).
Marrus, PR Newswire, Researchers Present First Preclinical Studies Suggesting Op-1 Can Protect Against Acute Renal Failure, Nov. 1996.
Marrus, PR Newswire, Creative Biomolecules' OP-1 Protects Against Kidney Damage in Models of Acute and Chronic Renal Failure, May 1996.

\* cited by examiner

Figure 1

Creatinine Levels (mg/dL)

|  | Vehicle (N=8) | OP-1 (N=7) |
|---|---|---|
| Day 0 | 0.55 | 0.57 |
| Day 2 | 3.69 | 3.56 |
| Day 4 | 2.78 | 1.59 |

Hemodynamic parameters (day 4)

|  | Vehicle (N=8) | OP-1 (N=7) |
|---|---|---|
| Renal blood flow | 5.23 | 7.97 |
| GFR (ml/min) | 0.453 | 0.731 |
| Urine flow (ul/min) | 10.6 | 16.0 |
| Blood pressure (mm Hg) | 119.5 | 119.9 |
| Heartrate (bpm) | 345 | 338.6 |

Figure 2

THERAPIES FOR ACUTE RENAL FAILURE

CROSS-REFERENCE TO RELATED APPLICATIONS

This application is a continuation of U.S. application Ser. No. 12/583,013, filed Aug. 11, 2009, which is a continuation of U.S. application Ser. No. 09/445,328, filed Dec. 7, 1999, now abandoned, which is a National Stage filing under 35 U.S.C. 371 of PCT International Application No. PCT/US98/03197, filed May 5, 1998, which claims the priority benefit of U.S. Provisional Application Ser. No. 60/045,619, filed May 5, 1997, all of which are hereby incorporated by reference in their entireties. International Application PCT/US98/03197 was published under PCT Article 21(2) in English.

SEQUENCE LISTING

The instant application contains a Sequence Listing which has been submitted in ASCII format via EFS-Web and is hereby incorporated by reference in its entirety. Said ASCII copy, created on Jun. 10, 2011, is named STK-P03-514 Sequence Listing and is 4.03 bytes in size.

FIELD OF THE INVENTION

The present invention relates generally to methods of treatment for renal disease and, in particular, methods of treatment for mammals, including humans, afflicted with, or at risk of, acute renal failure. The methods involve the administration of certain proteins of the osteogenic protein/bone morphogenetic protein (OP/BMP) family within the TGF-β superfamily of proteins.

BACKGROUND OF THE INVENTION

The mammalian renal system serves primary roles both in the removal of catabolic waste products from the bloodstream and in the maintenance of fluid and electrolyte balances in the body. Renal failure is, therefore, a life-threatening condition in which the build-up of catabolites to and other toxins, and/or the development of significant imbalances in electrolytes or fluids, may lead to the failure of other major organs systems and death. As a general matter, renal failure is classified as "acute" or "chronic" As detailed below, acute renal failure typically involves a rapid, drastic, life-threatening loss of renal function over a period of a few hours to several weeks. In contrast, chronic renal failure typically involves a slow, progressive loss of renal function over a period of months to years, during which time the subject's life is not immediately threatened.

Acute renal failure is characterized by an abrupt cessation or substantial reduction of renal function, and is typically diagnosed by relatively rapid increases in blood urea nitrogen (BUN) or serum creatinine levels over a period of a few hours or days. In as many as 90-95% of cases, acute renal failure may be secondary to trauma, surgery or another acute medical condition. Generally speaking, acute renal failure may be due to pre-renal, post-renal, or intrinsic renal causes. Pre-renal causes (e.g., decreased cardiac output, hypovolemia, altered vascular resistance) and post-renal causes (e.g., obstructions or constrictions of the ureters, bladder or urethra) do not involve direct damage to the kidneys but; by affecting the flow of blood to the kidneys or the flow of urine from the kidneys, may lead to significant permanent and/or progressive damage to renal tissues. On the other hand, acute renal failure may be due to intrinsic renal causes which involve a more direct insult or injury to the kidneys, and which also may entail permanent and/or progressive damage to the nephrons or other kidney structures. Intrinsic causes of acute renal failure include but are not limited to infectious diseases (e.g., various bacterial, viral or parasitic infections), inflammatory diseases (e.g., glomerulonephritis, systemic lupus erythematosus), ischemic (e.g., renal artery occlusion), toxic syndromes (e.g., heavy metal poisoning, side-effects of antimicrobial treatments or chemotherapy), and direct traumas.

In human acute renal failure patients, oliguria (urine output<400 ml/day) or anuria (urine output<50 ml/day) may be present in 50-70% of cases, BUN levels may climb 10-20 mg/dL/day or faster, plasma creatinine levels may climb 0.5-1.0 mg/dL/day, and metabolic acidosis is almost always present. If not treated, the electrolyte and fluid imbalances (e.g., hyperkalemia, acidosis, edema) associated with acute renal failure may lead to life-threatening arrhythmia, congestive heart failure, or multiple organ system failures. Due to the severity of acute renal failure, episodes rarely last longer than several weeks without mortality and are treated on an in-patient basis.

A need remains, therefore, for treatments which will prevent, inhibit, delay or alleviate the permanent or progressive loss of renal function which may result from acute renal failure.

SUMMARY OF THE INVENTION

The present invention is directed to methods of treatment, and pharmaceutical preparations for use in the treatment, of mammalian subjects in, or at risk of, acute renal failure. Such subjects include subjects already in acute renal failure, as well as any subject reasonably expected to suffer acute loss of renal function. Whether a particular subject is in acute renal failure, or is at risk of acute renal failure, is a determination which may routinely be made by one of ordinary skill in the relevant medical or veterinary art. Subjects in acute renal failure include those showing either (1) an increase in blood urea nitrogen (BUN) at a rate of at least 2 to 4 mmol/L/day (5 to 10 mg/dL/day), or (2) an increase in serum creatinine at a rate of at least 20 to 40 µmol/L/day (0.25 to 0.5 mg/dL/day). More typically, subjects in acute renal failure show rates of increase in BUN of at least 4 to 8 mmol/L/day (10 to 20 mg/dL/day), and rates of increase of serum creatinine of at least 40 to 80 µmol/L/day (0.5 to 1.0 mg/dL/day). Subjects "at risk" of acute renal failure include subjects which are reasonably expected to enter acute renal failure or which are otherwise expected to otherwise suffer a rapid progressive loss of renal function. Whether a particular subject is at risk is a determination which may routinely be made by one of ordinary skill in the relevant medical or veterinary art. Subjects at risk of acute renal failure include but are not limited to the following: (1) subjects in which serial determination of BUN indicates a rate of increase of at least 1 to 2 mmol/L/day (2.5 to 5 mg/dL/day); (2) subjects in which serial determination of serum creatinine indicates a rate of increase of at least 10 to 20 µmol/L/day (0.125 to 0.25 mg/dL/day); (3) subjects which have been diagnosed with a pre-renal cause of acute renal failure; (4) subjects which have been diagnosed with a post-renal cause of acute renal failure; and (5) subjects which have been diagnosed with an intrinsic renal cause of acute renal failure.

The methods and compositions of this invention capitalize in part upon the discovery that certain proteins of eukaryotic origin, defined herein as OP/BMP renal therapeutic agents, and including members of the osteogenic protein/bone morphogenetic protein (OP/BMP) family of proteins, may be used in the treatment of subjects in, or at risk of, acute renal failure. Useful renal therapeutic agents include polypeptides, or functional variants of polypeptides, comprising at least the C-terminal six- or seven-cysteine domain of a mammalian protein selected from the group consisting of OP-1, OP-2, OP-3, BMP2, BMP3, BMP4, BMP5, BMP6, BMP9, and proteins which exhibit at least 70% or, more preferably, 75% or 80% amino acid sequence homology with the amino acid sequence of the seven-cysteine domain of human OP-1; and which are (a) capable of inducing chondrogenesis in the Reddi-Sampath ectopic bone assay (Sampath and Reddi (1981), *Proc. Natl. Acad. Sci.* (*USA*) 78:7599-7603) or a substantially equivalent assay, (b) capable of significantly preventing, inhibiting, delaying or alleviating the permanent or progressive loss of renal function which may result from acute renal failure in a standard animal model of acute renal failure, or (c) capable of causing a clinically significant improvement in a standard marker of renal function when administered to a mammal in, or at risk of, acute renal failure.

The renal therapeutic agents of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and renal intracapsular. Administration is expected to be continuous or frequent (e.g., daily) during the period of acute renal failure, typically 1-3 weeks, but may also be continued for several weeks or months after the acute phase. Daily dosages of the renal therapeutic agents are expected to be in the range of about 0.01-1000 µg/kg body weight, and more preferably about 10-700 µg/kg body weight, although precise dosages will vary depending upon the particular renal therapeutic agent employed and the particular subject's medical condition and history.

The treatments of the present invention are useful in reducing the rate and/or degree of morbidity in mammals in, or at risk of, acute renal failure. In addition, the treatments of the present invention are useful in preventing, inhibiting, delaying or alleviating the permanent or progressive loss of renal function which may result from acute renal failure. As such, the present invention has great value, not only for increasing survival rates, but also in preventing or delaying the need for chronic dialysis or renal replacement therapy, in preventing or delaying the development of chronic renal insufficiency or chronic renal failure, and/or for reducing the necessary frequency of chronic renal dialysis.

In another aspect, the OP/BMP renal therapeutic agents of the invention are useful in reducing inflammation and neutrophil-mediated tissue damage. In this respect, the OP/BMP therapeutic agents are also shown to be useful in reducing the expression of ICAMs, particularly ICAM-1, when administered systemically. In particular, the OP/BMP therapeutics may be used to reduce ICAM expression in epithelial issue, particularly renal epithelium.

In yet another aspect, the OP/BMP renal therapeutic agents of the invention are useful for inhibiting apoptosis of cells in damaged or injured tissues. In this respect, the OP/BMP therapeutic agents are shown to reduce apoptosis of damaged or injured epithelial tissues, particularly renal epithelium.

In another aspect, the OP/BMP renal therapeutic agents of the invention may be used in the manufacture of medicaments for the treatment of any of the above-described conditions.

DETAILED DESCRIPTION OF THE INVENTION

I. Definitions

In order to more clearly and concisely point out the subject matter of the claimed invention, the following definitions are provided for specific terms used in the following written description and appended claims.

Acute Renal Failure.

Acute renal failure is typically defined as a rapid deterioration in renal function sufficient to result in the accumulation of nitrogenous wastes in the body (see, e.g., Anderson and Schrier (1994), in *Harrison's Principles of Internal Medicine,* 13th edition, Isselbacher et al., eds., MCGraw Hill Text, New York). Rates of increase in BUN of at least 4 to 8 mmol/L/day (10 to 20 mg/dL/day), and rates of increase of serum creatinine of at least 40 to 80 µmol/L/day (0.5 to 1.0 mg/dL/day), are typical in acute renal failure. In subjects which are catabolic (or hypercatabolic), rates of increase in BUN may exceed 100/mg/dL/day. Rates of increase in BUN or serum creatinine are usually determined by serial blood tests and, preferably, at least two blood tests are conducted over a period of between 6 and 72 hours or, more preferably, 12 and 24 hours. A distinction is sometime made between "acute" renal failure (deterioration over a period of days) and "rapidly progressive" renal failure (deterioration over a period of weeks). As used herein, however, the phrase "acute renal failure" is intended to embrace both syndromes.

Pre-Renal Causes of Acute Renal Failure.

As used herein, pre-renal causes of acute renal failure include decreased cardiac output, hypovolemia, volume redistribution, and altered vascular resistance.

Post-Renal Causes of Acute Renal Failure.

As used herein, post-renal causes of acute renal failure include ureteral, pelvic and bladder obstructions. For example, blood clots and kidney stones may cause obstructions of the ureters or bladder. Obstructions also may arise from sloughed papillae, and fungus balls. Extrinsic obstructions may result from, for example, malignancies or hypertrophies (e.g., prostatic or bladder carcinoma), retroperitoneal fibrosis, or iatrogenic causes (e.g., inadvertent ligation). Urethral strictures or phimosis may also cause pre-renal acute renal failure.

Intrinsic Renal Causes of Acute Renal Failure.

As used herein, intrinsic renal causes of acute renal failure include:

(1) Abnormalities of the vasculature such as vasoconstrictive disease (e.g., malignant hypertension, scleroderma, hemolytic uremic syndrome, thrombotic thrombocytopenic purpura) and vasculitis (e.g., polyarteritis nodosa, hypersensitivity angiitis, serum sickness, Wegener's granulomatosis, giant cell arteritis, mixed cryoglobulinemia, Henoch-Schönlein purpura, systemic lupus erythematosus);

(2) Abnormalities of the glomeruli such as post-infectious abnormalities (e.g., post-streptococcal, pneumococcal, gonococcal, staphylococcal, enterococcal, viral [e.g., hepatitis B and C, mumps, measles, Epstein-Barr], malarial, or related to brucellosis, *Legionella, Listeria*, shunt nephritis, leprosy, leptospirosis, or visceral abscesses) and non-infectious abnormalities (e.g., rapidly progressive glomerulonephritis, membranoproliferative glomerulonephritis, Goodpasture's syndrome, systemic lupus erythematosus, Wegener's granulomatosis);

(3) Acute interstitial nephritis resulting from drug related causes (e.g., penicillins, sulfonamides, carbenicillin, cephalosporin, erythromycin, nafcillin, oxacillin, nonsteroidal anti-inflammatory agents, diuretics [furosemide, ethacrynic acid, thiazide, spironolactone, mercurials], phenyloin, phenobarbital, probenicid, allopurinol, cimetidine), infection related causes (e.g., acute pyelonephritis, streptococcal, staphylococcal, leptospirosis, malaria, salmonellosis), papillary necrosis (e.g., associated with diabetes mellitus, sickle cell diseases, analgesic abuse, alcoholism), and other, miscellaneous causes (e.g., sarcoidosis, leukemia, lymphoma);

(4) Intratubular obstruction from crystal deposition (e.g., uric acid, oxalate, methotrexate) or multiple myeloma and light chain disease; and (5) Acute tubular necrosis resulting from nephrotoxins (e.g., antimicrobials such as aminoglycosides, tetracyclines, amphotericin, polymyxin, cephalosporins), heavy metals (e.g., mercury, lead, arsenic, gold salts, barium), and other, miscellaneous chemical agents (e.g., cisplatin, doxorubicin, streptozocin, methoxyflurane, halothane, ethylene glycol, carbon tetrachloride), or from ischemia (e.g., hemorrhage, hypotensibn, sepsis, burns, renal infarction, renal artery dissection, rhabdomyolysis, trauma), or other miscellaneous causes (e.g., contrast agents, transfusion reactions, myoglobinernia, heat stroke, snake and spider bites).

Other diseases and conditions which place a subject at risk of acute renal failure include: kidney transplantation surgery (as donor or recipient), bilateral arterial occlusion; bilateral acute renal vein thrombosis, acute uric acid nephropathy, hypovolemia, cardiovascular collapse, acute bilateral upper tract obstruction, hypercalcemic nephropathy, hemolytic uremic syndrome, acute urinary retention, malignant nephrosclerosis, essential mixed cyroimmunoglobulinemia, oxalate nephropathy, cortical necrosis, postpartum glomerulosclerosis, hypersensitivity nephropathy, scleroderma, idiopathic rapidly progressive glomerulonephritis, Goodpasture's syndrome, non-Goodpasture's anti-GBM disease, acute bacterial endocarditis or visceral sepsis, microscopic polyarteritis nodosa, Wegener's granulomatosis, allergic granulomatosis, acute radiation nephritis, post-streptococcal glomerulonephritis, nonstreptococcal post-infectious glomerulonephritis, diffuse proliferative lupus nephritis, membranoproliferative glomerulonephritis, renal vein thrombosis, Waldenstrom's macroglobulinemia, multiple myeloma, Berger's (IgA) nephropathy, Henoch-Schönlein purpura, and focal glomerulosclerosis.

OP/BMP Renal Therapeutic Agent.

As used herein, the terms "OP/BMP renal therapeutic to agent," "renal therapeutic agent of the invention," and the like mean a polypeptide, or a functional variant of a polypeptide, comprising at least the C-terminal six- or seven-cysteine domain of a mammalian protein selected from the group consisting of OP-1, OP-2, OP-3, BMP2, BMP3, BMP4, BMP5, BMP6, BMP9, and proteins which exhibit at least 70% or, more preferably, 75% or 80% amino acid sequence homology with the amino acid sequence of the seven-cysteine domain of human OP-1; and which is (a) capable of inducing chondrogenesis in the Reddi-Sampath ectopic bone assay (Sampath and Reddi (1981), *Proc. Natl. Acad. Sci.* (USA) 78:7599-7603) or a substantially equivalent assay, (b) capable of significantly preventing, inhibiting, delaying or alleviating the permanent or progressive loss of renal function which may result from acute renal failure in a standard animal model of acute renal failure, or (c) capable of causing a clinically significant improvement in a standard marker of renal function when administered to a mammal in, or at risk of, acute renal failure.

Therapeutic Efficacy.

As used herein, a renal therapeutic agent of the invention is said to have "therapeutic efficacy," and an amount of the agent is said to be "therapeutically effective," if administration of that amount of the agent is sufficient to cause a clinically significant improvement in a standard marker of renal function when administered to a mammalian subject (e.g., a human patient) in, or at risk of, acute renal failure. Such markers of renal function are well known in the medical literature and include, without being limited to, rates of increase in BUN levels, rates of increase in serum creatinine, static measurements of BUN, static measurements of serum creatinine; glomerular filtration rates (GFR), ratios of BUN/creatinine, serum concentrations of sodium (Na+), urine/plasma ratios for creatinine, urine/plasma ratios for urea, urine osmolality, daily urine output, and the like (see, for example, Anderson and Schrier (1994), in *Harrison's Principles of Internal Medicine,* 13th edition, Isselbacher et al., eds., McGraw Hill Text, New York; Kumar and Stein (1994), in *Internal Medicine,* 4th Edition, J. H. Stein, ed., Mosby-Year Book, Inc. St. Louis.)

II. Embodiments of the Invention

A. General

The present invention depends, in part, upon the surprising discovery that administration of certain protein-based renal therapeutic agents to subjects in acute renal failure, or at risk of acute renal failure, can reduce mortality and/or morbidity rates, and prevent, inhibit, delay or alleviate the permanent and/or progressive loss of renal function associated with acute renal failure. The present invention is particularly surprising in light of the fact that the agents of the present invention are proteins, whereas standard treatment regimes for acute renal failure include the limitation of protein intake to reduce strain on the kidneys. In preferred embodiments, the to renal therapeutic agents of the invention are members of the osteogenic protein/bone morphogenetic protein (OP/BMP) family within the TGF-β superfamily of proteins.

B. OP/BMP Renal Therapeutic Agents

The renal therapeutic agents of the present invention are naturally occurring proteins, or functional variants of naturally occurring proteins, in the osteogenic protein/bone morphogenetic protein (OP/BMP) family within the TGF-β superfamily of proteins. That is, these proteins form a distinct subgroup, referred to herein as the "OP/BMP family," within the loose evolutionary grouping of sequence-related proteins known as the TGF-β superfamily. Members of this protein family comprise secreted polypeptides that share common structural features, and that are similarly processed from a pro-protein to yield a carboxy-terminal mature protein. Within the mature protein, all members share a conserved pattern of six or seven cysteine residues defining a 97-106 amino acid domain, and the active form of these proteins is either a disulfide-bonded homodimer of a single family member, or a heterodimer of two different members (see, e.g., Massague (1990), *Annu. Rev. Cell Biol.* 6:597; Sampath et al. (1990), *J. Biol. Chem.* 265:13198). For example, in its mature, native form, natural-sourced human OP-1 is a glycosylated dimer typically having an apparent molecular weight of about 30-36 kDa as determined by SDS-PAGE. When reduced, the 30 kDa protein gives rise to two glycosylated peptide subunits having apparent molecular weights of about 16 kDa and 18 kDa. The unglycosylated protein has an apparent molecular weight of about 27 kDa. When reduced, the 27 kDa protein gives rise to two unglycosylated polypeptide chains, having molecular weights of about 14 kDa to 16 kDa.

Typically, the naturally occurring OP/BMP proteins are translated as a precursor, having an N-terminal signal peptide sequence, a "pro" domain, and a "mature" protein domain. The signal peptide is typically less than 30 residues, and is cleaved rapidly upon translation at a cleavage site that can be predicted using the method of Von Heijne (1986), *Nucleic Acids Research* 14:4683-4691. The "pro" domain is variable both in sequence and in length, ranging from approximately 200 to over 400 residues. The pro domain is cleaved to yield the "mature" C-terminal domain of approximately 115-180 residues, which includes the conserved six- or seven-cysteine C-terminal domain of 97-106 residues. As used herein, the "pro form" of an OP/BMP family member refers to a protein comprising a folded pair of polypeptides, each comprising a pro domain in either covalent or noncovalent association with the mature domains of the OP/BMP polypeptide. Typically, the pro form of the protein is more soluble than the mature form under physiological conditions. The pro form appears to be the primary form secreted from cultured mammalian cells. The "mature form" of the protein refers to mature C-terminal domain which is not associated, either covalently or noncovalently, with the pro domain. Any preparation of OP-1 is considered to contain mature form when the amount of pro domain in the preparation is no more than 5% of the amount of "mature" C-terminal domain.

OP/BMP family members useful herein include any of the known naturally-occurring native proteins including allelic, phylogenetic counterpart and other variants thereof; whether naturally-sourced or biosynthetically produced (e.g., including "muteins" or "mutant proteins"), as well as new, active members of the OP/BMP family of proteins.

Particularly useful sequences include those comprising the C-terminal seven cysteine domains of mammalian, preferably human, OP-1, OP-2, OP-3, BMP2, BMP3, BMP4, BMP5, BMP6, BMP8 and BMP9. Other proteins useful in the practice of the invention include active forms of GDF-5, GDF-6, GDF-7, DPP, Vg1, Vgr-1, 60A, GDF-1, GDF-3, GDF-5, GDF-6, GDF-7, BMP10, BMP11, BMP13, BMP15, UNIVIN, NODAL, SCREW, ADMP or NURAL and amino acid sequence variants thereof. In one currently preferred embodiment, the renal therapeutic agents of the invention are selected from any one of: OP-1, OP-2, OP-3, BMP2, BMP3, BMP4, BMP5, BMP6, and BMP9.

Publications disclosing these sequences, as well as their chemical and physical properties, include: OP-1 and OP-2: U.S. Pat. No. 5,011,691, U.S. Pat. No. 5,266,683, and Ozkaynak et al. (1990), *EMBO J.* 9:2085-2093; OP-3: WO94/10203; BMP2, BMP3, and BMP4: U.S. Pat. No. 5,013,649, WO91/18098, WO88/00205, and Wozney et al. (1988), *Science* 242:1528-1534; BMP5 and BMP6: WO90/11366 and Celeste et al. (1991), *Proc. Natl. Acad. Sci.* (*USA*) 87:9843-9847; Vgr-1: Lyons et al. (1989), *Proc. Natl. Acad. Sci.* (*USA*) 86: 4554-4558; DPP: Padgett et al. (1987), *Nature* 325:81-84; Vg1: Weeks (1987), *Cell* 51:861-867; BMP-9: WO95/33830; BMP 10: WO94/26893; BMP-11: WO94/26892; BMP12: WO95/16035; BMP-13: WO95/16035; GDF-1: WO92/00382 and Lee et al. (1991), *Proc. Natl. Acad. Sci.* (*USA*) 88:4250-4254; GDF-8: WO94/21681; GDF-9: WO94/15966; GDF-10: WO95/10539; GDF-11: WO96/01845; BMP-15: WO96/36710; MP121: WO96/01316; GDF-5 (CDMP-1, MP52): WO94/15949, WO96/14335, WO93/16099 and Storm et al. (1994), *Nature* 368:639-643; GDF-6 (CDMP-2, BMP13): WO95/01801, WO96/14335 and WO95/10635; GDF-7 (CDMP-3, BMP12): WO95/10802 and WO95/10635; BMP-3b: Takao, et al. (1996), *Biochem. Biophys. Res. Comm.* 219:656-662; GDF-3: WO94/15965; 60A: Blaster et al. (1993), *Cell* 73:687-702 and GenBank accession number L12032. In another embodiment, useful proteins include biologically active biosynthetic constructs, including novel biosynthetic proteins and chimeric proteins designed using sequences from two or more known OP/BMP family proteins. See also the biosynthetic constructs disclosed in U.S. Pat. No. 5,011,691, the disclosure of which is incorporated herein by reference (e.g., COP-1, COP-3, COP-4, COP-5, COP-7, and COP-16).

In other preferred embodiments, the renal therapeutic agents useful herein include therapeutically effective proteins in which the amino acid sequences comprise a sequence sharing at least 70% amino acid sequence "homology" and, preferably, 75% or 80% homology with the C-terminal seven cysteine domain present in the active forms of human OP-1 (i.e., residues 330-431, as shown in SEQ ID NO: 2 of U.S. Pat. No. 5,266,683). In other preferred to embodiments, the renal therapeutic agents useful herein include therapeutically effective proteins in which the amino acid sequences comprise a sequence sharing at least 60% amino acid sequence identity and, preferably, 65% or 70% identity with the C-terminal seven cysteine domain present in the active forms of human OP-1. As will be understood by those skilled in the art, homologous or functionally equivalent sequences include functionally equivalent arrangements of the cysteine residues within the conserved cysteine skeleton, including amino acid insertions or deletions which alter the linear arrangement of these cysteines, but do not materially impair their relationship in the folded structure of the dimeric protein, including their ability to form such intra- or inter-chain disulfide bonds as may be necessary for biological activity. To determine the degree of homology of a candidate amino acid sequence to the C-terminal seven cysteine skeleton of human OP-1, the candidate sequence and the reference sequence are first aligned using an alignment algorithm, such as the dynamic programming algorithm described in Needleman et al., *J. Mol. Biol.* 48:443 (1970), or the Align Program, a commercial software package produced by DNAstar, Inc., the teachings of which are incorporated by reference herein. After the initial alignment is made, it may then be refined by comparison to the sequences of other members of the OP/BMP family of related proteins. Once the alignment between the candidate and reference sequences is made and refined, a percent homology score is calculated. The individual amino acids of each sequence are compared sequentially according to their similarity to each other. Similarity factors include similar size, shape and electrical charge. One particularly preferred method of determining amino acid similarities is the PAM250 matrix described in Dayhoff et al. (1978), *Atlas of Protein Sequence and Structure* Vol. 5 (Suppl. 3), pp. 354-352, Natl. Biomed. Res. Found., Washington, D.C., incorporated by reference herein. A similarity score is first calculated as the sum of the aligned pair-wise amino acid similarity scores. Insertions and deletions are ignored for the purposes of percent homology and identity. Accordingly, gap penalties are not used in this calculation. The raw score is then normalized by dividing it by the geometric mean of the scores of the candidate compound and the seven cysteine skeleton of hOP-1. The geometric mean is the square root of the product of these scores. The normalized raw score is the percent homology.

Thus, amino acid sequence "homology" is understood herein to include both amino acid sequence identity and similarity and, as used herein, a percentage "homology" between two amino acid sequences indicates the percentage of amino acid residues which are identical or similar between the sequences. "Similar" residues are "conservative substitutions" which fulfill the criteria defined for an "accepted point mutation" in Dayhoff et al. (1978), supra. Thus, "conservative substitutions" are residues that are physically or functionally similar to the corresponding reference residues, having similar size, shape, electric charge, and/or chemical properties such as the ability to form covalent or hydrogen bonds, or the like. Examples of conservative substitutions include the substitution of one amino acid for another with similar to characteristics, e.g., substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine. The term "conservative substitution" or "conservative variation" also includes the use of a substituted amino acid in place of an unsubstituted parent amino acid in a given polypeptide chain, provided that the resulting substituted polypeptide chain also has therapeutic efficacy in the present invention.

The renal therapeutic agents of the invention are also characterized by biological activities which may be readily ascertained by those of ordinary skill in the art. Specifically, a renal therapeutic agent of the present invention is (a) capable of inducing chondrogenesis in the Reddi-Sampath ectopic bone assay (Sampath and Reddi (1981), *Proc. Natl. Acad. Sci.* (*USA*) 78:7599-7603) or a substantially equivalent assay, (b) capable of significantly preventing, inhibiting, delaying or alleviating the permanent or progressive loss of renal function which may result from acute renal failure in a standard animal model of acute renal failure, or (c) capable of causing a clinically significant improvement in a standard marker of renal function when administered to a mammal in, or at risk of, acute renal failure.

The Reddi-Sampath ectopic bone assay is well known in the art as an assay of chondrogenic activity. The assay, which can be easily performed, is described and discussed in, for example, Sampath and Reddi (1981), *Proc. Natl. Acad. Sci.* (*USA*) 78:7599-7603; and Wozney (1989), "Bone Morphogenetic Proteins," *Progress in Growth Factor Research* 1:267-280. Many equivalent assays, using other animals and tissue sites, may be employed or developed by those of skill in the art to evaluate the biological activity of the renal therapeutic agents of the present invention. See, for example, the bioassays described in U.S. Pat. No. 5,226,683.

The renal therapeutic agents of the present invention also may be tested in animal models of acute renal failure. Mammalian models of acute renal failure in, for example, mice, rats, guinea pigs, cats, dogs, sheep, goats, pigs, cows, horses, and non-human primates, may be created by causing an appropriate direct or indirect injury or insult to the renal tissues of the animal. Animal models of acute renal failure may, for example, be created by inducing in the animal the conditions or diseases described above as placing a subject "at risk" of acute renal failure. In particularly preferred embodiments, an animal model is employed in which acute renal failure is induced by the controlled administration of nephrotoxic agents (e.g., cisplatin, aminoglycoside antibiotics, heavy metals).

Finally, the renal therapeutic agents of the present invention may be evaluated for their therapeutic efficacy in causing a clinically significant improvement in a standard marker of renal function when administered to a mammalian subject (e.g., a human patient) in, or at risk of, acute renal failure. Such markers of renal function are well known in the medical literature and include, without being limited to, rates of increase in BUN levels, rates of increase in serum creatinine, to static measurements of BUN, static measurements of serum creatinine, glomerular filtration rates (GFR), ratios of BUN/creatinine, serum concentrations of sodium (Na+), urine/plasma ratios for creatinine, urine/plasma ratios for urea, urine osmolality, daily urine output, and the like (see, for example, Anderson and Schrier (1994), in *Harrison's Principles of Internal Medicine,* 13th edition, Isselbacher et al., eds., McGraw Hill Text, New York; Kumar and Stein (1994), in *Internal Medicine,* 4th Edition, J. H. Stein, ed., Mosby-Year Book, Inc. St. Louis).

The renal therapeutic agents contemplated herein can be expressed from intact or truncated genomic or cDNA or from synthetic DNAs in prokaryotic or eukaryotic host cells. The dimeric proteins can be isolated from the culture media and/or refolded and dimerized in vitro to form biologically active compositions. Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including *E. coli,* or eukaryotes including yeast, *Saccharomyces,* insect cells, or mammalian cells, such as CHO, COS or BSC cells. One of ordinary skill in the art will appreciate that other host cells can be used to advantage. Detailed descriptions of the proteins useful in the practice of this invention, including how to make, use and test them for chondrogenic activity, are disclosed in numerous publications, including U.S. Pat. Nos. 5,266,683 and 5,011,691, the disclosures of which are herein incorporated by reference.

C. Subjects for Treatment

As a general matter, the methods of the present invention may be utilized for any mammalian subject in, or at risk of, acute renal failure. Mammalian subjects which may be treated according to the methods of the invention include, but are not limited to, human subjects or patients. In addition, however, the invention may be employed in the treatment of domesticated mammals which are maintained as human companions (e.g., dogs, cats, horses), which have significant commercial value (e.g., dairy cows, beef cattle, sporting animals), which have significant scientific value (e.g., captive or free specimens of endangered species), or which otherwise have value. In addition, as a general matter, the subjects for treatment with the methods of the present invention need not present indications for treatment with the agents of the invention other than those associated with acute renal failure or risk of acute renal failure. That is, the subjects for treatment may be otherwise free of indications for treatment with the agents of the invention. In some number of cases, however, the subjects may present with other symptoms (e.g., osteodystrophy) for which renal therapeutic agent treatment would be indicated. In such cases, the renal therapeutic agent treatment should be adjusted accordingly so to avoid excessive dosing.

One of ordinary skill in the medical or veterinary arts is trained to recognize subjects in, or to at risk of, acute renal failure, and a detailed scientific literature has developed around the subject. See, for example, Anderson and Schrier (1994), in *Harrison's Principles of Internal Medicine,* 13th edition, Isselbacher et al., eds., McGraw Hill Text, New York; Kumar and Stein (1994), in *Internal Medicine,* 4th Edition, J. H. Stein, ed., Mosby-Year Book, Inc. St. Louis.

Preferably, a diagnosis that a subject is in acute renal failure, or at risk of entering acute renal failure, is made on the basis of serial blood tests measuring, among other factors, the circulating levels of serum creatinine and blood urea nitrogen. Such "serial" blood tests may be taken every few hours immediately upon admittance of an undiagnosed patient presenting with symptoms of acute renal failure. More typically, however, consecutive serial blood tests are separated by a period of at least 6 hours, not more than 72 hours, and preferably 12-24 hours. On the basis of two or more blood tests within a 24 or 72 hour period, it is possible to calculate a rate of increase of serum creatinine or BUN.

Finally, it should be noted that subjects possessing a single kidney, irrespective of the manner of loss of the other kidney (e.g., physical trauma, surgical removal, birth defect), may be considered to be at increased risk of acute renal failure. This is particularly true for those subjects in which one kidney has been lost due to a disease or condition which may afflict the remaining kidney. Similarly, subjects which are already recipients of a renal transplant, or which are receiving chronic dialysis (e.g., chronic hemodialysis or continuous ambulatory peritoneal dialysis) may be considered to be at increased risk of acute renal failure. Therefore, for these subjects, the clinical indications discussed above may need to be more carefully monitored, and earlier or more aggressive intervention with renal therapeutic agent treatment may be advisable.

In another aspect, the OP/BMP renal therapeutic agents of the invention are useful in reducing inflammation and neutrophil-mediated tissue damage. This is demonstrated in Example 3, below, in which it is seen that systemically administered OP-1 reduces inflammation, the accumulation and activity of neutrophils, and neutrophil-mediated damage in a rat ischemia-reperfusion injury model of ARF. Thus, the OP/BMP therapeutic agents are shown to be useful in reducing inflammation, the accumulation and activity of neutrophils, and neutrophil-mediated damage in injured or damaged epithelial tissue, and particularly renal epithelial tissue. In this same respect, the OP/BMP therapeutic agents are also shown to be useful in reducing the expression of ICAMs, particularly ICAM-1, when administered systemically. Thus, the OP/BMP therapeutics are shown to be useful in reducing ICAM expression in epithelial issue, particularly renal epithelial tissue.

In yet another aspect, the OP/BMP renal therapeutic agents of the invention are useful for inhibiting apoptosis of cells in damaged or injured tissues. This is also demonstrated in Example 3, below, in which it is seen that systemically administered OP-1 reduces the number of apoptotic cells in a rat ischemia-reperfusion injury model of ARF. Thus, the OP/BMP therapeutic agents are shown to be useful in inhibiting apoptosis of damaged or injured epithelial tissues, particularly to renal epithelium.

D. Formulations and Methods of Treatment

The renal therapeutic agents of the present invention may be administered by any route which is compatible with the particular renal therapeutic agent employed. Thus, as appropriate, administration may be oral or parenteral, including intravenous, intraperitoneal, and renal intracapsular routes of administration. In addition, administration may be by periodic injections of a bolus of the renal therapeutic agent, or may be made more continuous by intravenous or intraperitoneal administration from a reservoir which is external (e.g., an i.v. bag) or internal (e.g., a bioerodible implant or implanted pump).

The renal therapeutic agents of the invention may be provided to an individual by any suitable means, preferably directly (e.g., locally, as by injection or topical administration to a tissue locus) or systemically (e.g., parenterally or orally). Where the agent is to be provided parenterally, such as by intravenous, subcutaneous, or intramuscular, administration, the agent preferably comprises part of an aqueous solution. The solution is physiologically acceptable so that in addition to delivery of the desired agent to the subject, the solution does not otherwise adversely affect the subject's electrolyte and/or volume balance. The aqueous medium for the agent thus may comprise normal physiologic saline (e.g., 9.85% NaCl, 0.15M, pH 7-7.4).

If desired, a given renal therapeutic agent or other agent may be made more soluble by association with a suitable molecule. For example, association of a mature OP/BMP dimer with an OP/BMP pro domain results in the pro form of the renal therapeutic agent which typically is more soluble or dispersible in physiological solutions than the corresponding mature form. In fact, endogenous members of the OP/BMP family are thought to be transported (e.g., secreted and circulated) in the mammalian body in this form. This soluble form of the protein can be obtained from culture medium of OP/BMP-secreting mammalian cells, e.g., cells transfected with nucleic acid encoding and competent to express the protein. Alternatively, a soluble species can be formulated by complexing the mature dimer (or an active fragment thereof) with a pro domain or a solubility-enhancing fragment thereof (described more fully below). Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990.

Alternatively, the agents described herein may be administered orally. Oral administration of proteins as therapeutics generally is not practiced as most proteins are readily degraded by digestive enzymes and acids in the mammalian digestive system before they can be absorbed into the bloodstream. However, the renal therapeutic agents described herein typically are acid stable to and protease-resistant (see, for example, U.S. Pat. No. 4,968,590). In addition, at least one of these renal therapeutic agents, OP-1, has been identified in mammary gland extract, colostrum and 57-day milk. Moreover, the OP-1 purified from mammary gland extract is therapeutically efficacious and also is detected in the bloodstream. Finally; soluble form OP-1, e.g., mature OP-1 associated with the pro domain, is therapeutically efficacious. These findings, as well as those disclosed in the examples below, indicate that oral and parenteral administration are viable means for administering the renal therapeutic agents of the invention to an individual. In addition, while the mature forms of certain renal therapeutic agents described herein typically are sparingly soluble, the form found in milk (and mammary gland extract and colostrum) is readily soluble, probably by association of the mature, therapeutically efficacious form with part or all of the pro domain of the intact sequence and/or by association with one or more milk components: Accordingly, the compounds provided herein also may be associated with molecules capable of enhancing their solubility in vitro or in vivo.

The compounds provided herein also may be associated with molecules capable of targeting the renal therapeutic agent to the desired tissue. For example, an antibody, antibody fragment, or other binding protein that interacts specifically with a surface molecule on cells of the desired tissue, may be used. Useful targeting molecules may be designed, for example, using the single chain binding site technology disclosed, for example, in U.S. Pat. No. 5,091,513.

As will be appreciated by one of ordinary skill in the art, the formulated compositions contain therapeutically effective amounts of the renal therapeutic agent. That is, they contain amounts which provide appropriate concentrations of the agent to the renal tissues for a time sufficient to prevent, inhibit, delay or alleviate permanent or progressive loss of renal function, or otherwise provide therapeutic efficacy. As will be appreciated by those skilled in the art, the concentration of the compounds described in a therapeutic composition of the present invention will vary depending upon a number of factors, including the biological efficacy of the selected agent, the chemical characteristics (e.g., hydrophobicity) of the compounds employed, the formulation of the compound excipients, the administration route, and the treatment envisioned, including whether the active ingredient will be administered directly into a kidney or renal capsule, or whether it will be administered systemically. The preferred dosage to be administered also is likely to depend on such variables such as the condition of the renal tissues, extent of renal function loss, and the overall health status of the particular subject. Dosages are preferably administered continuously, but daily, multi-weekly, weekly or monthly dosages may also be employed. For subjects which would otherwise require continuous, bi-weekly or tri-weekly hemodialysis sessions, continuous, bi-weekly or tri-weekly intravenous or intraperitoneal infusions are not considered unduly inconvenient. In addition, in order to facilitate frequent infusions, implantation of a semi-permanent stent (e.g., intravenous, intraperitoneal or intracapsular) may be advisable.

The renal therapeutic agents of the invention may, of course, be administered alone or in combination with other molecules known to be beneficial in the treatment of the conditions described herein. When used in combination with other agents, it may be advisable to alter the dosages of the renal therapeutic agents of the present invention accordingly.

Thus, in another aspect, the present invention provides for the use of the OP/BMP renal therapeutic agents of the invention in the manufacture of medicaments for the treatment of any of the above-described conditions.

Practice of the invention, including additional preferred aspects and embodiments thereof, will be still more fully understood from the following examples, which are presented herein for illustration only and should not be construed as limiting the invention in any way.

Example 1

Figure 1:
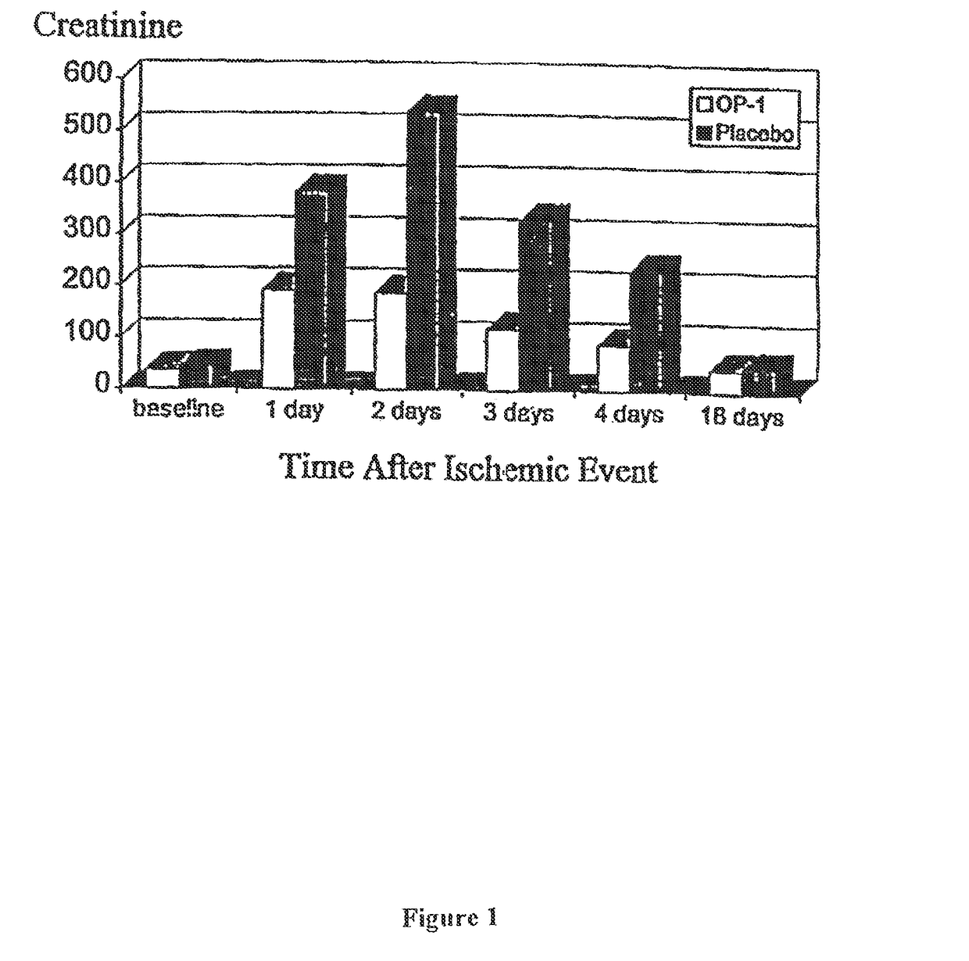
FIG. 1 is a bar graph showing the effect of OP-1 on creatinine levels in rats in which ischemic renal damage was induced by temporarily preventing renal blood flow. The vertical axis of the graph is a scale of creatinine (µmol/L).

To examine the ability of OP-1 to beneficially affect the course of renal function after an acute ischemic insult to the kidney, the effect of OP-1 on creatinine levels was examined in rats in which ischemic renal damage was induced by temporarily preventing renal blood flow. In this model system, both renal arteries are clamped for 60 minutes. OP-1 is administered into the tail vein of each rat at 0.25 µg/kg at the following four times: 10 minutes before artery clamping, and then again at each of 24, 48, and 72 hours after the ischemic injury. As shown in FIG. 1, the creatinine level of placebo-treated rats rises rapidly after injury, peaks at the 24 hour measurement, and is back to normal by the 18th day post-injury. In contrast, OP-1 treatment is associated with a creatinine level which peaks at the 24 hour measurement to a level only half that of the placebo group, after which it begins to decrease. For each of the four post-injury days on which measurements were made, the creatinine level of the placebo treated rats was at least twice as high as that of the OP-1 treated animals. These results indicate that OP-1 may limit the damage caused to renal tissue by an ischemic insult, and may also speed the functional recovery of the kidney.

Example 2

To study the effect of post-injury OP-1 treatment on renal function in another animal model of renal failure, rats with a single kidney were with OP-1 2 days after norepinephrine-induced renal damage. In the model system (further described in Conger et al., *Kidney Intl.* 40:21-28, 1991), each rat has a kidney removed 7 days prior to renal injury, which is induced by intra-arterial infusion of norepinephrine for 90 minutes. Two days after norepinephrine administration, OP-1 is administered intravenously at 0.25 mg/kg.

Figure 2:
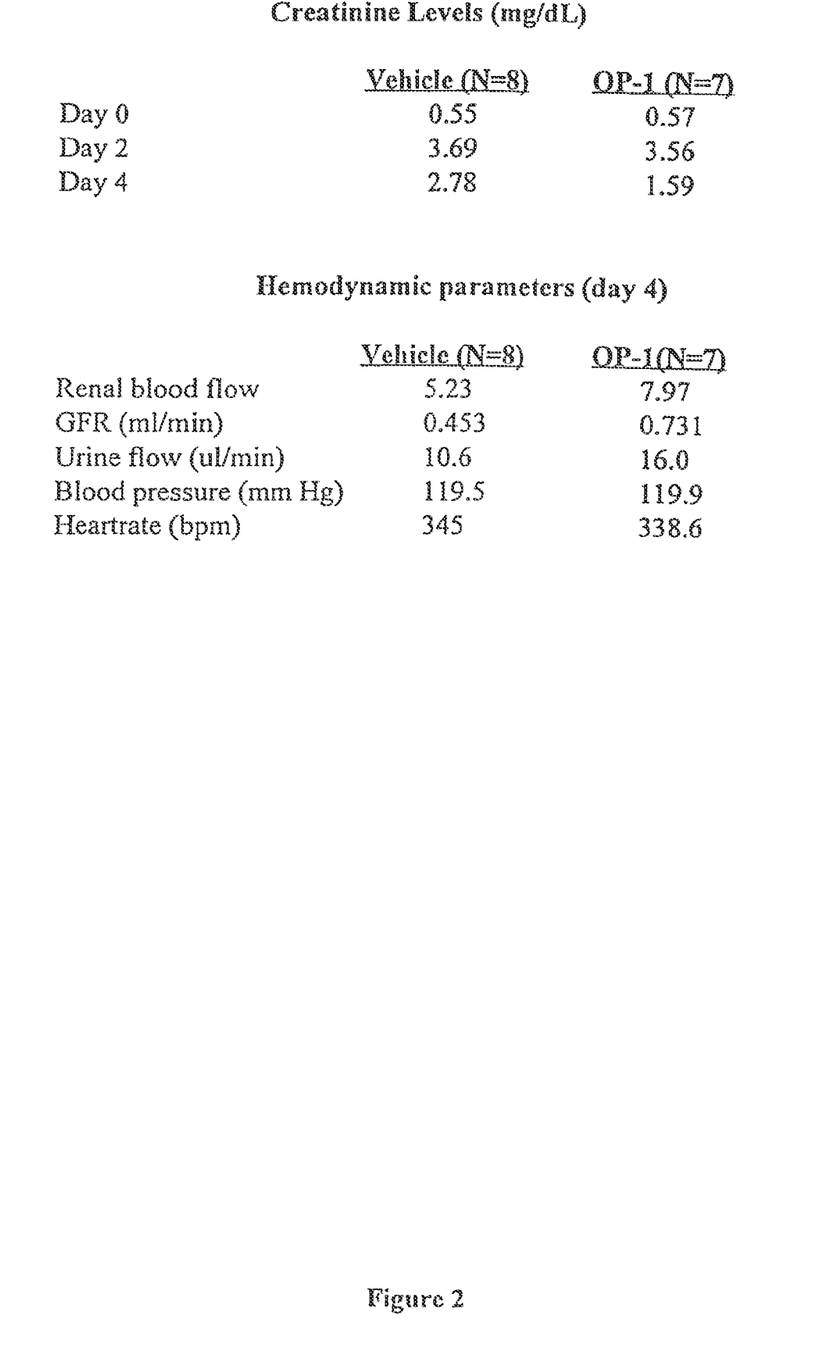
FIG. 2 is a table showing the effect of OP-1 on creatinine levels and on hemodynamic parameters in rats in which renal function was impaired by administering norepinephrine.

The upper table of FIG. 2 presents creatinine levels of vehicle- and OP-1 treated rats. On the fourth day after injury, the animals which had been treated with OP-1 on the second day after injury had creatinine levels which are significantly lower than the levels of the vehicle-treated controls. The data presented in the lower table of FIG. 2 shows that OP-1 treatment was also associated with improvements in renal blood flow, GFR, and urine flow as compared to controls.

Example 3

Further experiments, using ischemic-reperfusion injury as a model of acute renal failure in rats, were conducted as follows:

Animal Surgical Procedures and Experimental Protocols.

Wistar male rats of 200-250 g (Pliva Breeding Laboratory, Zagreb, Croatia) were fasted for 12 h prior to surgery. After intraperitoneal administration of ketamin (20 mg/kg) anesthetic, both renal arteries were dorsally occluded for 60 minutes with microaneurysm clamps (Roboz). Vehicle buffer or OP-1 containing 20 mM sodium acetate buffer (5000) were administered via the tail vein. All animals were subjected to intraperitoneal administration of 1-3 ml of pre-warmed (37° C.) saline (0.9% NaCl) to compensate for any fluid loss during the surgery. Experiments were blind, and rats were terminated at different time intervals ranging from 30 min to 18 days. Blood samples (0.5 ml) were obtained from the orbital plexus at 0 h, 24 h, 48 h, and 72 h and, in some cases, at 30 min, 2 h, 8 h, and 96 h, and 18 days following reperfusion. For GFR measurements, urine was collected from metabolic cages for 24 h as previously described (Vukicevic et al. (1989) *Bone Miner,* 6:125-39). Serum and urine creatinine was measured by the Jaffe method (Whelton et al. (1994) in *Clinical Chemistry,* Burtis and Ashwood, eds., Amer. Assn. Clin. Chem.), blood urea nitrogen (BUN) was measured by glutamate dehydrogenase UV procedure, phosphorus was measured by a molybdate method, and calcium was measured by an o-cresolphtaleine method. Serum electrolytes were measured by indirect potentiometry. Fifteen independent experiments with a total of 456 rats were performed. In a prophylactic model, OP-1 was administered 10 minutes prior to surgery and then at 24 h, 48 h, and 72 h thereafter. In a therapeutic model, the first OP-1 injection was administered either at 1 h or 16 h after reperfusion, followed by injections at 24 h intervals up to 96 h following reperfusion.

Histomorphometry and Immunocytochemistry

At sacrifice, each kidney was split longitudinally and one half was fixed in 4% paraformaldehyde. Two consecutive sections from paraffin embedded blocks were stained with H&E and PAS. The morphometric measurements were done on longitudinal sections using an eye-piece grid that contains 100-point grid lines under a Nikon microscope (Nikon Optiphot-2; MVI, Avon, Mass.). The grid was calibrated by a stage micrometer and the area of a specific feature was measured by counting the number of intersects (points or hits) that were superimposed on the tissue of interest. All counts were done through a 1× objective lens. Each point or hit represents an area of 0.61 mm². Verification of features were done at a higher magnification, if they could not be discerned through the 1× objective lens.

Morphometric variables included total tissue area, dilated tubular area, plugged tubular area, infarcted area, and necrotic area. A dilated tubule was defined as a tubular structure having distended lumen and identifiable epithelial cells. A plugged tubule was defined as a tubular structure having debris-filled lumen and identifiable epithelial cells. An infarcted area was defined as a portion or a zone of the kidney showing identifiable tissue profiles and lost cellular details, which was stained bright pink by H&E stain, and which was associated with regional congestion in the outer medulla. A necrotic area was defined as a portion or a zone of the kidney located in the infarcted area showing loss of both tissue profits and cellular details.

Immunocytochemistry was performed using the immunoperoxidase detection system (Zymed, San Francisco, Calif.). The following monoclonal antibodies were used: PCNA (proliferating cell nuclear antigen; Dako, Denmark), smooth muscle α-actin (SMA) (Dako, Denmark), smooth muscle myosin IgG (BTI, Stoughton, Mass.) and ICAM (CD 54; Dako, Denmark). A minimum of 3000 cells were counted per kidney section stained for PCNA and SMA, and the number of positive cells was expressed as a percentage of total counted cells in the subdivisions of cortex, and/or $S_3$ zone.

Apoptotic cells were detected by a TACS 2 TdT in situ apoptosis system (Trevigen, Gaithersburg, Md.). The total number of apoptotic cells were counted in cortex and medulla in three sections per kidney from eight independent animals per group, sacrificed at days 1, 2, 3, and 5 following reperfusion.

Neutrophil Accumulation and Activity

The neutrophil infiltration was determined using naphthol AS-D chloroacetate esterase staining (Sigma) on histologic sections. The neutrophils were counted in the cortex and $S_3$ zone (outer medulla and inner cortex) using an ocular grid. Data were expressed as number of neutrophils per mm², evaluated on 100 high power fields per section, two sections per animal from 8 independent rats at 24 h following injury. In addition, neutrophil activity was determined at 24 h following injury by myeloperoxidase activity (MPO). For MPO, kidneys were extracted in 0.5% HTAB (Sigma) in 50 mM $KPO_4$ buffer, pH 6.0, homogenized for 10 min, sonicated for 5 min and, finally, the lysate was centrifuged for 60 min at 20,000× g. Ten μl of extract was incubated with 1 ml of 50 mM $KPO_4$ buffer containing 0.167 mg/ml O-dianisidine (Sigma) and 0.0005% $H_2O_2$ at 25° C. Absorbance was determined at 460 nm using a myeloperoxidase standard (Oxis) and normalized to kidney wet weight.

Statistical Analysis

Two way analysis of variance and post hoc analysis with Duncan's multiple range test were performed to determine the effects of treatment and time on biochemical and histological parameters. Mann-Whitney-U tests & Chi-tests were used to determine the significance of differences in results between selected groups.

Prophylactic and Therapeutic Effects

In a typical experiment, at 24 h post reperfusion, serum creatinine (Cr) and blood urea nitrogen (BUN) levels were increased 8 to 10 times above normal values in rats with acute renal failure that received vehicle acetate buffer (500 μl; pH 4.5). Intravenous injection of 250 μg OP-1/kg at 10 minutes prior to clamping and then at 24 h intervals up to 72 h post reperfusion, dramatically decreased the mortality rate and strongly suppressed the elevation of serum Cr, BUN, phosphorus and potassium values, as compared to vehicle-treated rats. Serum sodium and chloride values were unchanged in all animals. Vehicle alone did not influence the kidney function in rats with ARF as compared to ARF rats that received none. The OP-1 dose which successfully protected the kidney against ischemic injury varied with age of the animal and severity of ischemia and reperfusion, and was within a range of 50-250 μg/kg. GFR measured at 24 h after reperfusion was significantly higher in OP-1 treated rats than in vehicle-treated rats. Specifically, sham rats had a GFR (ml/min) of 4.7±0.8; vehicle-treated ARF rats had a GFR of 0.25±0.11; and OP-1 treated rats had a GFR of 0.45±0.17 ($p<0.05$ vs ARF). To examine the therapeutic potential of OP-1 for the treatment of established ARF, OP-1 was administered either at 1 h or 16 h following reperfusion. Both OP-1 treatment groups showed lower serum Cr and BUN values. The reduction of serum Cr and BUN was more dramatic in rats with OP-1 administered at 1 h than those receiving OP-1 at 16 h post reperfusion. These results indicate that OP-1 protects against loss of kidney function in ischemia as measured by serum biochemical parameters.

Protection Against Kidney Damage

Histological analysis of kidney sections from rats with ARF indicated that morphologic changes had occurred in the $S_3$ zone. At 2 h after reperfusion, vehicle treated kidneys showed signs of congestion which led to large areas of parenchymal infarction and necrosis when examined at 24 h, 72 h, and 120 h after reperfusion. Animals given OP-1 prior to ischemia, however, exhibited little or no congestion and had less infarction; 28 of 32 vehicle-treated kidneys and 16 of 32 OP-1 treated kidneys had white infarction (necrosis), and 26 of 32 vehicle-treated and 14 of 32 OP-1 treated rats had red infarction. Histomorphometric analyses showed that 6 and 11% of the kidney section area in vehicle-treated rats and 0 and 0.3% of OP-1 treated rats had white or red infarction, respectively. In the kidney area affected by infarction, approximately 50% of tubules were dilated both in vehicle and OP-1 treated rats at 1 to 5 days following injury. However, fewer tubules plugged with desquamated epithelial cells, cell debris, and cast matrix were found in OP-1 treated rats as compared with vehicle-treated animals on days 2 and 5 post injury. The analysis of peritubular capillary-derived smooth muscle cells revealed that at 24 h post-injury, approximately 5-fold more cells in the $S_3$ zone of OP-1 treated kidneys expressed α-actin as compared to vehicle treated kidneys, suggesting that OP-1 therapy supports the maintenance of a vascular smooth muscle phenotype. Cell proliferation evaluated by PCNA staining indicated an increase in proximal tubule cell growth in the cortex and outer medulla of OP-1 treated rats. In animals treated 1 h after reperfusion, OP-1 had a similar protective action on kidney histology. In animals treated 16 h after reperfusion, the structural damage was similar to vehicle-treated animals at 24 h following injury.

Suppression of Inflammation

As ICAM-1 has been reported to play an important role during the onset of ARF, we determined the effect of OP-1 on the expression of ICAM-1 at different time points following ischemia and reperfusion. OP-1 treatment 10 min prior to ischemia attenuated the expression of ICAM-1 as determined by molecular and histochemical analyses of kidneys obtained at 30 min, 2 h and 8 h following reperfusion. Significant neutrophil accumulation in vehicle-treated rats was observed at 24 h following reperfusion in the $S_3$ zone. In contrast, rats treated with OP-1 had dramatically decreased neutrophil accumulation (232±47 cells/mm$^2$ in vehicle vs 9±3 cells/mm$^2$ in OP-1 group; n=8, p<0.01). Neutrophil activity in the kidney was monitored by measuring the total tissue myeloperoxidase activity (MPO). Administration of OP-1 1 h following reperfusion decreased the MPO activity approximately 3-fold as determined at 24 h post reperfusion (MPO/μg/wet kidney: 37.3±16.5 in vehicle vs 12.8±7.6 in OP-1 treated kidneys; n=8; p<0.01).

Reduction of Apoptosis

At days 1 and 2 following injury, there were no differences in the number of apoptotic cells in the medulla of both OP-1 and vehicle-treated kidneys. However, a reduction in the number of apoptotic cells was observed in the cortex of OP-1 treated rats. Five days after injury, OP-1 treatment resulted in a dramatic reduction of apoptotic cells attached to the basement membrane of tubules of both the cortex and medulla, whereas numerous apoptotic cells were observed in the lumen of the renal tubules of vehicle-treated rats.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

---

What is claimed is:

1. A method for treating a mammal in acute renal failure comprising administering to said mammal a therapeutically effective amount of OP-1, wherein said acute renal failure has an intrinsic renal cause selected from the group consisting of abnormalities of the vasculature and post-infectious abnormalities of the glomeruli.

2. The method of claim 1 wherein said mammal is undergoing renal dialysis treatment and wherein said administration of OP-1 reduces the frequency of said dialysis treatments.

3. The method of claim 1 or 2 wherein said OP-1 is selected from the group consisting of a pro form, a mature form, and a soluble form.

4. The method of claim 1 wherein said mammal is a kidney transplant recipient.

5. The method of claim 1 or 2 wherein said administration is selected from oral, parenteral, intravenous, intraperitoneal, or into the renal capsule.

6. The method of claim 5 wherein a stent has been implanted into said mammal for said administration.

7. The method of claim 6 wherein said stent is selected from an intravenous stent, an intraperitoneal stent, or a renal intracapsular stent.

8. The method of claim 1 or 2 wherein said OP-1 is administered at a dosage of about 0.01-1000 µg/kg body weight of said mammal or 0.1-100 µg/kg body weight of said mammal.

* * * * *

SEQUENCE LISTING

<160> NUMBER OF SEQ ID NOS: 1

<210> SEQ ID NO 1
<211> LENGTH: 431
<212> TYPE: PRT
<213> ORGANISM: Homo sapiens

<400> SEQUENCE: 1

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
        130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Glu Arg Ile
                180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
        210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255
```

-continued

```
Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
            290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430
```